United States Patent [19]

Saddler et al.

[11] Patent Number: 5,079,371

[45] Date of Patent: Jan. 7, 1992

[54] PROCESS FOR PRODUCTION OF PROSTAGLANDIN INTERMEDIATES

[75] Inventors: John C. Saddler, Portage; John H. Symonds, Vicksburg, both of Mich.

[73] Assignee: Upjohn Company, Kalamazoo, Mich.

[21] Appl. No.: 487,975

[22] PCT Filed: Jul. 12, 1988

[86] PCT No.: PCT/US88/02293

§ 371 Date: Mar. 1, 1990

§ 102(e) Date: Mar. 1, 1990

[87] PCT Pub. No.: WO89/01936

PCT Pub. Date: Mar. 9, 1989

Related U.S. Application Data

[63] Continuation-in-part of Ser. No. 92,957, Sep. 4, 1987, abandoned.

[51] Int. Cl.$^5$ .................................... C07D 307/935
[52] U.S. Cl. .................................................. 549/312
[58] Field of Search ........................................ 549/312

[56] References Cited

U.S. PATENT DOCUMENTS 4,013,695  3/1977  Lin .................................... 260/408

Primary Examiner—Jane T. Fan
Attorney, Agent, or Firm—Bruce Stein

[57] ABSTRACT

The present invention is a process for the production of a ketolactone of formula III

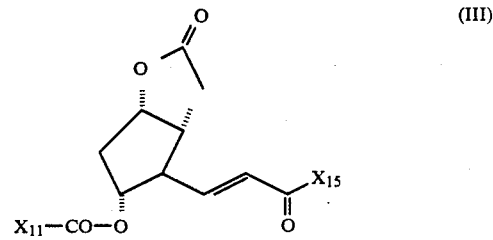

which comprises contacting an aldehyde lactone of formula I

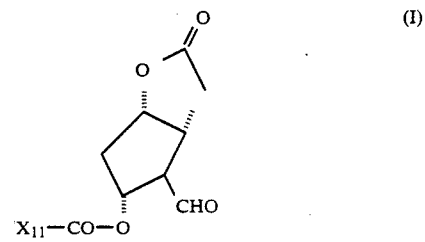

with a β-ketophosphonate $(X_1-O-)_2-PO-CH_2-CO-X_{15}$ (II). The ketolactone (III) is a useful intermediate in the synthesis of prostaglandins.

14 Claims, No Drawings 5,079,371

PROCESS FOR PRODUCTION OF PROSTAGLANDIN INTERMEDIATES

CROSS-REFERENCE TO RELATED APPLICATIONS

The present patent application is the national phase patent application of PCT/US88/02293, filed Jul. 11, 1988 which was a continuation-in-part application of U.S. patent application Ser. No. 092,957, filed Sept. 4, 1987 (now abandoned).

BACKGROUND OF THE INVENTION

1. Field of the Invention

The present invention is a process for the condensation of a bicyclic lactone containing an aldehyde function at what is known as the $C_{12}$ position of a prostaglandin (I), with a β-ketophosphonate (II) to form a known ketolactone (III) which is a useful intermediate in the synthesis of prostaglandins.

2. Description of the Related Art

The aldehyde lactone (I) containing the aldehyde function at what is known as the $C_{12}$ position of a prostaglandin is well known to those skilled in the art. It is known as the "Corey Aldehyde".

Reaction of the (protected) Corey aldehyde with a ketophosphonate anion, producing a prostaglandin intermediate, is what is known as the Emmons reaction. This reaction is well known, see U.S. Pat. Nos. 4,210,669, 4,212,811, 4,191,823 and 4,321,275. These patents report yields of 13.4, 14.7, 44, about 60, 64 and 90%.

The Corey Aldehyde is known to be quite unstable, eliminating to the enal, see J. Am. Chem. Soc., 96, 5855 (1974) and Tet. Letters, 3275 (1976) particularly under basic conditions (potassium carbonate/methanol), see Tet. Letters, 1319 (1973). This elimination reaction is what is generally responsible for the poor yields of the Emmons reaction.

It would be highly desireable to be able to react the Corey aldehyde (I) with the appropriate reagent in a Wittig Reaction to produce the desired side chain at $C_{12}$ in the β configuration. The problem is that the Corey Aldehyde (I) gives substantial elimination; 10-50%, to the enal under standard conditions.

The use of lithium chloride and an amine in a Horner-Wadsworth-Emmons reaction involving base sensitive readily epimerizable aldehydes is known, see Tet. Letters, 25, 2183 (1984). The addition of the aldehyde to a premixed phosphonate-lithium chloride-amine mixture is disclosed. While the aldehydes were known to be readily epimerizable, they differ from the aldehydes of the present invention in that the aldehyde lactones (I) do not epimerize in base but rather eliminate to the enal. The fact that readily epimerizable aldehydes did not epimerize is no indication that readily eliminatable aldehydes would not eliminate. The fact that epimerizable aldehydes did not epimerize only demonstrates that the bases involved (trialkylamines) are not basic enough to deprotonate (enolize) a carbonyl compound; the $pK_a$ of the conjugate acid was greater than approximately 16 to 18. As explained in "Advanced Organic Chemistry—Part A" second edition, by F. A. Corey and R. J. Sundberg in Chapter 6, there is a "continuum of mechanistic possibilities" for the elimination reaction ranging from an E1cb type with initial deprotonation followed by loss of the leaving group, which would require a strong base, to an E1 type with initial ionization of the leaving group followed by proton loss in which "the base plays no role in the rate determining step". For elimination reactions one must consider both the base and the leaving group; use of a non-epimerizing base for the Wittig reaction does not guarantee elimination will be prevented in a system prone to elimination (a system with a good leaving group). In fact, if the Wittig reaction is greatly slowed by use of too weak a base so that the elimination prone aldehyde is not rapidly converted but exposed to the basic system, elimination may actually be promoted.

The use of triethylamine as the amine in the Horner-Wadsworth-Emmons reactions using simple, stable aldehydes was disclosed in J. Org. Chem., 50, 2624 (1985).

The reaction of a more complex aldehyde and a phosphonate in the presence of lithium chloride and DBU provides the enone product in only 35-60% yield with recovery of 35-50% aldehyde, see J. Am. Chem. Soc., 107, 3731 (1985).

It has been discovered that if the appropriate β-ketophosphonate (II) to produce the desired ketolactone (III) is contacted with a lithium or magnesium salt, a trialkylamine and the aldehyde lactone (I), the ketolactone is produced in excellent yields.

SUMMARY OF INVENTION

Disclosed is a process for the production of a ketolactone of formula (III) where $X_{15}$ is —$CH_2$—O—ϕ where —ϕ is optionally substituted with —Cl or —$CF_3$ in the meta position,
—$CH_2$—$CH_2$—ϕ where —ϕ is optionally substituted with —Cl or —$CF_3$ in the meta position,
—$C(CH_3)_3$,
—$(CH_2)_4$—$CH_3$,
—$C(CH_3)_2$—$(CH_2)_3$—$CH_3$,
—$CH_2$—$CH(CH_3)$—$(CH_2)_n$—$CH_3$ where n is 2 or 3,
—$C(CH_3)_2$—$CH_2$—O—$CH_2$—$CH_3$,
cyclopentyl and
cyclohexyl, which comprises (1) contacting an aldehyde lactone of formula (I) with a β-ketophosphonate ($X_1$—O—$)_2$—PO—$CH_2$—CO—$X_{15}$ (II) where $X_1$ is $C_1$-$C_4$ alkyl, —ϕ or —$CH_2$—ϕ and where $X_{15}$ is as defined above, in the presence of a lithium or magnesium salt and a trialkylamine.

DETAILED DESCRIPTION OF THE INVENTION

It has been discovered that if a β-ketophosphonate (II) is contacted with a lithium or magnesium salt, a trialkylamine and an aldehyde lactone (I), the corresponding ketolactone (III) is produced in excellent yield.

The aldehyde lactones (I) are known, see JACS 91, 5675 (1969), ibid 93, 1491 (1971) and 96, 5865 (1974).

The β-ketophosphonates (II) are known, see JACS 90, 3247 (1968) for $X_1$ as —$CH_3$ and $X_{15}$ as —$(CH_2)_4$—$CH_3$ and the general method for β-ketophosphonate preparation.

Suitable lithium or magnesium salts include LiCl, LiBr, LiI, $MgCl_2$, $MgBr_2$, and $MgI_2$. Preferred are LiCl, LiBr, LiI, $MgCl_2$ and $MgBr_2$. More preferred is LiCl, LiBr and $MgBr_2$.

Trialkylamines include $NR_1R_2R_3$. Preferred trialkylamines include triethylamine, 1,8-diazabicyclo[5.4.0]undec-7-ene, 1,1,3,3-tetramethylguanidine and diisopropylethylamine. More preferred is triethylamine.

The aldehyde lactone (I) can be added to the mixture of the β-ketophosphonate (II)+lithium or magnesium salt+trialkylamine or the mixture can be added to the aldehyde. It is possible to add the trialkylamine base to the mixture of the lithium or magnesium salt, aldehyde lactone (I) and β-ketophosphonate (II). It is preferred that the aldehyde lactone (I) be added to the β-ketophosphonate (II) mixture and be added slowly over 30–45 minutes. The aldehyde can be added neat or in a non-polar solvent. Suitable solvents include, for example, methylene chloride, THF, acetonitrile or mixtures thereof. The temperature of the reaction mixture when the aldehyde lactone (I) is contacted with the β-ketophosphonate (II) mixture is not critical, suitable temperature range is from about −40° to about 65°, preferably about −20° to about 25°.

The reaction mixture is stirred until the reaction is complete as measured by TLC or HPLC. The reaction is usually complete in about 3 to about 6 hr. The ketolactone (III) is isolated and purified by means known to those skilled in the art.

The ketolactones (III) are known useful intermediates in the production of pharmaceutically useful prostaglandins, see JACS 96, 5865 (1974) and Prostaglandins and Thromboxanes, R. F. Newton and S. M. Roberts (1982).

The ketolactones (III) of the present invention are intermediates in the production of prostaglandins. After the side chain at what is known as $C_{12}$ of the prostaglandin is added to the aldehyde lactone (I) by the process of the present invention, the side chain at $C_8$ is added by known chemistry. The numbering system used in identifying the variable substituents (except in the EXAMPLES) is that of the final product prostaglandins as will be apparent to one skilled in the art. The double bond at $C_{13}$ and $C_{14}$ is in the trans configuration.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3-C(=Z_1)H$. Groups $R_i$ and $R_j$ would represent monovalent variable substituents if attached to the formula $CH_3-CH_2-C(R_i)(R_j)H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as prostaglandins, these carbon atoms are designated as $C_i$, where "i" is the integer corresponding to the carbon atom number. For example, $C_9$ represents the 9 position or carbon atom number in the prostaglandin nucleus as traditionally designated by those skilled in the art of prostaglandin chemistry. Likewise the term "$R_9$" represents a variable substituent (either monovalent or bivalent) at the $C_9$ position.

Chemical formulas or portions thereof drawn in a linear fashion represent atoms in a linear chain. The symbol "—" in general represents a bond between two atoms in the chain. Thus $CH_3-O-CH_2-CH(R_i)-CH_3$ represents a 2-substituted-1-methoxypropane compound. In a similar fashion, the symbol "=" represents a double bond, e.g., $CH_2=C(R_i)-O-CH_3$, and the symbol "≡" represents a triple bond, e.g., $HC\equiv C-CH(R_i)-CH_2-CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by $N^*=C(CH_3)-CH=CCl-CH=C^*H$ with the convention that the atoms marked with an asterisk (*) are bonded to each other resulting in the formation of a ring. Likewise, the cyclic molecular fragment, 4-(ethyl)-1-piperazinyl can be represented by $-N^*-(CH_2)_2-N(C_2H_5)-CH_2-C^*H_2$.

A cyclic (ring) structure for any compound herein defines an orientation with respect to the plane of the ring for substituents attached to each carbon atom of the cyclic compound. In formulas depicting such compounds, a substituent attached to a carbon atom below the plane of the ring is identified as being in the alpha (α) configuration and is indicated by a broken, dashed or dotted line attachment to the carbon atom, i.e., by the symbol "- - -" or ". . .". The corresponding substituent attached above the plane of the ring is identified as being in the beta (β) configuration.

When a variable substituent is bivalent, the valences may be taken together or separately or both in the definition of the variable. For example, a variable $R_i$ attached to a carbon atom as $-C(=R_i)-$ might be bivalent and be defined as oxo or keto (thus forming a carbonyl group (—CO—) or as two separately attached monovalent variable substituents $\alpha$-$R_{i \cdot j}$ and $\beta$-$R_{i \cdot k}$. When a bivalent variable, $R_i$, is defined to consist of two monovalent variable substituents, the convention used to define the bivalent variable is of the form "$\alpha$-$R_{i \cdot j}$:$\beta$-$R_{i \cdot k}$" or some variant thereof. In such a case both $\alpha$-$R_{i \cdot j}$ and $\beta$-$R_{i \cdot k}$ are attached to the carbon atom to yield $-C(\alpha$-$R_{i \cdot j})(\beta$-$R_{i \cdot k})-$. For example, when the bivalent variable $R_6$, $-C(=R_6)-$ is defined to consist of two monovalent variable substituents, two monovalent variable substituents are $\alpha$-$R_{6 \cdot 1}$:$\beta$-$R_{6 \cdot 2}$, . . . $\alpha$-$R_{6 \cdot 9}$:$\beta$-$R_{6 \cdot 10}$, etc, yielding $-C(\alpha$-$R_{6 \cdot 1})(\beta$-$R_{6 \cdot 2})-$, . . . $-C(\alpha$-$R_{6 \cdot 9})(\beta$-$R_{6 \cdot 10})-$, etc. Likewise, for the bivalent variable $R_{11}$, $-C(=R_{11})-$, two monovalent variable substituents are $\alpha$-$R_{11 \cdot 1}$:$\beta$-$R_{11 \cdot 2}$. For a ring substituent for which separate $\alpha$ and $\beta$ orientations do not exist (e.g. due to the presence of a carbon carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula —C$_1$(R$_i$)H—CH$_2$(R$_j$)H— (C$_1$ and C$_2$ define arbitrarily a first and second carbon atom, respectively) R$_i$ and R$_j$ may be defined to be taken together to form (1) a second bond between C$_1$ and C$_2$ or (2) a bivalent group such as oxa (—O—) and the formula thereby describes an epoxide. When R$_i$ and R$_j$ are taken together to form a more complex entity, such as the group -X-Y-, then the orientation of the entity is such that C$_1$ in the above formula is bonded to X and C$_2$ is bonded to Y. Thus, by convention the designation "... R$_i$ and R$_j$ are taken together to form —CH$_2$—CH$_2$—O—CO—..." means a lactone in which the carbonyl is bonded to C$_2$. However, when designated "... R$_j$ and R$_i$ are taken together to form —CH$_2$—CH$_2$—O—CO— the convention means a lactone in which the carbonyl is bonded to C$_1$.

The carbon atom content of variable substituents is indicated in one of two ways. The first method uses a prefix to the entire name of the variable such as "C$_1$-C$_4$", where both "1" and "4" are integers representing the minimum and maximum number of carbon atoms in the variable. The prefix is separated from the variable by a space. For example, "C$_1$-C$_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus C$_2$-C$_4$ alkoxycarbonyl describes a group CH$_3$—(CH$_2$)$_n$—O—CO— where n is zero, one or 2. By the second method the carbon atom content of only each portion of the definition is indicated separately by enclosing the "Ci-Cj" designation in parentheses and placing it immediately (no intervening space) before the portion of the definition being defined. By this optional convention (C$_1$-C$_3$)alkoxycarbonyl has the same meaning as C$_2$-C$_4$ alkoxycarbonyl because the "C$_1$-C$_3$" refers only to the carbon atom content of the alkoxy group. Similarly while both C$_2$-C$_6$ alkoxyalkyl and (C$_1$-C$_3$)alkoxy(C$_1$-C$_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

II. DEFINITIONS

All temperatures are in degrees Centigrade.
TLC refers to thin-layer chromatography.
HPLC refers to high pressure liquid chromatography.
THF refers to tetrahydrofuran.
DBU refers to 1,8-diazabicyclo[5.4.0]undec-7-ene.
DBN refers to 1,5-diazabicyclo[3.4.0]non-5-ene.
TEA refers to triethylamine.
TMG refers to 1,1,3,3-tetramethylguanidine.
DABCO refers to 1,4-diazabicyclo[2.2.2]octane.
DIPEA refers to diisopropylethylamine.
φ refers to phenyl (C$_6$H$_5$).
When solvent pairs are used, the ratios of solvents used are volume/volume (v/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

(-)-5α-(Benzoyloxy)-3,3aβ,4,5,6,6aβ-hexahydro-4β-(3-oxo-4-phenoxy-1E-butenyl)-2H-cyclopenta-[b]furan-2-one (III)

Dimethyl(2-oxo-3-phenoxylpropyl)phosphonate (II, 2.824 g) in THF (10 ml) is added to dry lithium chloride (0.464 g) followed by a rinse with THF (10 ml). Triethylamine (1.061 g) is added as a solution in THF (10 ml) followed by a rinse of THF (2 ml). The mixture is cooled to 10° and a solution of (-)-5α-(benzoyloxy)-4β-formyl-3,3aβ,4,5,6,6aβ-hexahydro-2H-cyclopenta[b]furan-2-one (I, 2.500 g) in methylene chloride 10 ml) is added dropwise over 30–45 minutes followed by a rinse of methylene chloride (2 ml). The reaction is stirred at 10° until complete (3–6 hr by TLC or HPLC). The reaction mixture is then diluted with methylene chloride (20 ml), extracted with hydrochloric acid (1N, 2×20 ml), dried over sodium sulfate and concentrated under reduced pressure to an oil. The oil is chromatographed on silica gel eluting with an ethyl acetate/hexane gradient. The appropriate fractions are pooled and concentrated to give the title compound; HPLC Rt 5.73 min on 5μsilica gel at 1 ml/min with methanol/methyl t-butyl ether (1/99) at 230 nm.

EXAMPLE 2

(-)-5α-(Benzoyloxy)-3,3aβ,4,5,6,6aβ-hexahydro-4β-(3-oxo-1E-octenyl)-2H-cyclopenta-[b]furan-2-one (III)

Following the general procedure of EXAMPLE 1 and making non-critical variations but using dimethyl(2-oxo-n-heptyl)phosphonate (II, 3.889 g), the title compound is obtained; TLC R$_f$=0.54 ethyl acetate/hexane (50/50).

EXAMPLE 3

(-)-5α-(Benzoyloxy)-3,3aβ,4,5,6,6aβ-hexahydro-4β-(4,4-dimethyl-3-oxo-1E-octenyl)-2H-cyclopenta-[b]furan-2-one (III)

Following the general procedure of EXAMPLE 1 and making non-critical variations but using dimethyl(3,3-dimethyl-2-oxo-n-heptyl)-phosphonate (II, 4.38 g), the title compound is obtained; TLC R$_f$=0.72 ethyl acetate/hexane (50/50).

EXAMPLES 4–14

(-)-5α-(Benzoyloxy)-3,3aβ,4,5,6,6aβ-hexahydro-4β-(3-oxo-4-phenoxy-1E-butenyl)-2H-cyclopenta-[b]furan-2-one (III)

Following the general procedure of EXAMPLE 1 and making noncritical variations but making the changes identified in TABLE 1, the title compound is obtained. TABLE 1 is found in CHART B.

CHART A

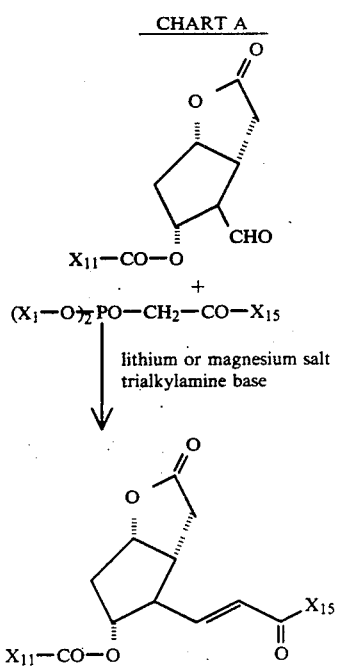

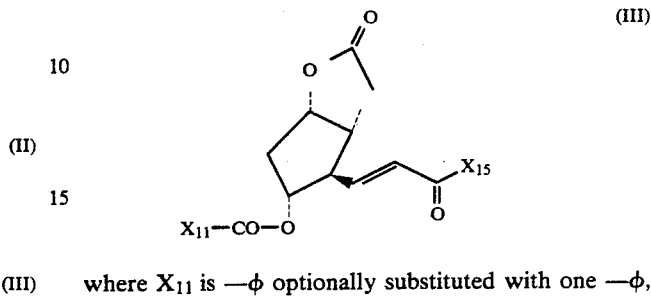

TABLE 1
CHART B

| EXAMPLE | Salt | Base | Add last | Solvent | Temp | HPLC R$_f$* |
|---|---|---|---|---|---|---|
| 4 | LiCl | DBU | lactone | CH$_3$CN | 20–25° | 5.25 min |
| 5 | LiCl | DIPEA | lactone | CH$_3$CN | 20–25° | 5.25 min |
| 6 | LiCl | TMG | lactone | CH$_3$CN | 20–25° | 5.31 min |
| 7 | LiCN | TEA | lactone | CH$_3$CN | 20–25° | 5.31 min |
| 8 | LiCl | TMG | lactone | THF | 20–25° | 5.49 min |
| 9 | LiCl | TEA | lactone | THF | 20–25° | 5.43 min |
| 10 | LiCl | TEA | lactone | THF | 0° | 5.42 min |
| 11 | LiCl | TEA | lactone | THF | −20° | 5.43 min |
| 12 | LiBr | TEA | lactone | THF | 20–25° | 5.48 min |
| 13 | LiI | TEA | lactone | THF | 20–25° | 5.50 min |
| 14 | LiCl | TEA | base | THF | 10° | 4.74 min |

*5μ silica gel column eluted with methanol/methyl t-butyl ether (1/99) at 1 ml/min at 254 nm

CHART C
BICYCLICLACTONE refers to

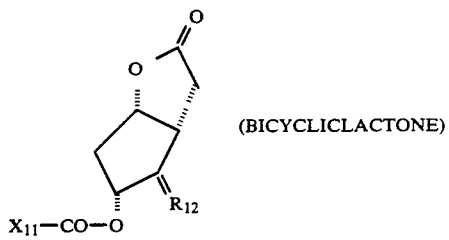

(BICYCLICLACTONE)

where
$X_{11}$ is $C_1$–$C_5$ alkyl, —CFH$_2$, —CF$_3$, —CClH$_2$, —CCl$_3$, —CH$_2$—φ, —CH$_2$—φ—φ, —CH$_2$—O—φ, —CH$_2$—O—φ—4—Cl, or φ optionally substituted with one —φ, —O—φ, —F, —Cl, —Br, —I, —CH$_3$, —O—CH$_3$; two —F, —Cl, —Br, —I, —CH$_3$, —O—CH$_3$ or three —CH$_3$, —O—CH$_3$, for the aldehyde lactone (I), R$_{12}$ is α—H:β—CHO,
for the ketolactone (III), R$_{12}$ is α—H:β—CH=CH—CO—X$_{15}$ where the double bond between C$_{13}$ and C$_{14}$ is in the trans configuration.

We claim:
1. A process for the production of a ketolactone of formula III

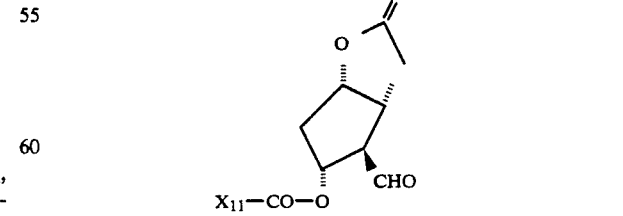

where X$_{11}$ is —φ optionally substituted with one —φ, —O—φ, —F, —Cl, —Br, —I, —CH$_3$, —O—CH$_3$; two —F, —Cl, —Br, —I, —CH$_3$, —O—CH$_3$ or three —CH$_3$, —O—CH$_3$, X$_{15}$ is —CH$_2$—O—φ where —φ is optionally substituted with —Cl or —CF$_3$ in the meta position,
—CH$_2$—CH$_2$—φ where —φ is optionally substituted with —Cl or —CF$_3$ in the meta position,
—C(CH$_3$)$_3$,
—(CH$_2$)$_4$—CH$_3$,
—C(CH$_3$)$_2$—(CH$_2$)$_3$—CH$_3$,
—CH$_2$—CH(CH$_3$)—(CH$_2$)$_n$—CH$_3$ where n is 2 or 3,
—C(CH$_3$)$_2$—CH$_2$—O—CH$_2$—CH$_3$,
cyclopentyl and
cyclohexyl, which comprises
(1) contacting an aldehyde lactone of formula (I)

(I)

where X$_{11}$ is a defined above, with a β-ketophosphonate of formula (II), $(X_1-O-)_2-PO-CH_2-CO-X_{15}$ (II)

where $X_1$ is $C_1$-$C_4$ alkyl, —$\phi$ or —$CH_2$—$\phi$ and where $X_{15}$ is as defined above, in the presence of a lithium or magnesium salt and a trialkylamine.

2. A process according to claim 1, where the lithium or magnesium salt is LiCl, LiBr, LiI, MgCl$_2$, MgBr$_2$ or MgI$_2$.

3. A process according to claim 1, where the salt is LiCl, LiBr or MgBr$_2$.

4. A process according to claim 1, where the salt is LiCl.

5. A process according to any preceding claim, where the trialkylamine is selected from DBN, DABCO, DBU, TMG, N-methylpiperidine, N,N-dimethylpiperazine, N-methylmorpholine, N-methylpyrrolidine, N,N-tetramethylethylenediamine, NR$_1$R$_2$R$_3$ and NR$_1$R$_2\phi$ where R$_1$, R$_2$ and R$_3$ are each C$_1$-C$_4$ alkyl.

6. A process according to claim 5, where the trialkylamine is triethylamine, DBU, TMG or diisopropylethylamine.

7. A process according to claim 5, where the trialkylamine is triethylamine.

8. A process according to any preceding claim, which is conducted at −40° to 65° C.

9. A process according to claim 8, which is conducted at −20° to 25° C.

10. A process according to any preceding claim, which is conducted in a solvent selected from methylene chloride, THF, acetonitrile and mixtures thereof.

11. A process according to claim 10, where the solvent is methylene chloride or THF or a mixture thereof.

12. A process according to any preceding claim, where $X_{15}$ is —$CH_2$—O—$\phi$, —$(CH_2)_4$—$CH_3$, —$C(CH_3)_2$—$(CH_2)_3$—$CH_3$ or —$CH_2$—$CH(CH_3)$—$(CH_2)_3$—$CH_3$.

13. A process according to claim 12, where the ketolactone (III) is selected from (-)-5α-(benzoyloxy)-3,3α$\beta$,4,5,6,6α$\beta$-hexahydro-4$\beta$-(3-oxo-4-phenoxy-1E-butenyl)-2H-cyclopenta[b]furan-2-one, (-)-5α-(benzoyloxy)-3,3α$\beta$,4,5,6,6α$\beta$-hexahydro-4$\beta$-(3-oxo-1E-octenyl)-2H-cyclopenta[b]furan-2-one, and (-)-5α-(benzoyloxy)-3,3α$\beta$,4,5,6,6α$\beta$-hexahydro-4$\beta$-(4,4-dimethyl-3-oxo-1E-octenyl)-2H-cyclopenta[b]furan-2-one.

14. A process for the production of a ketolactone of formula (III) according to claim 1 where $X_{11}$ is —$\phi$.

* * * * *